(12) United States Patent
Schneider et al.

(10) Patent No.: US 6,585,955 B1
(45) Date of Patent: *Jul. 1, 2003

(54) LONG-LASTING AQUEOUS DISPERSIONS OR SUSPENSIONS OF PRESSURE-RESISTANT GAS-FILLED MICROVESICLES AND METHODS FOR THE PREPARATION THEREOF

(75) Inventors: Michel Schneider, Troinex (CH); Feng Yan, Geneva (CH); Pascal Grenier, deceased, late of Ambilly (FR), by Nadine Garcel, legal heir; Jérôme Puginier, Valleiry (FR); Marie-Bernadette Barrau, Geneva (CH)

(73) Assignee: Bracco International B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/740,653

(22) Filed: Oct. 31, 1996

Related U.S. Application Data

(62) Division of application No. 08/380,588, filed on Jan. 30, 1995, now Pat. No. 5,578,292, which is a division of application No. 07/991,237, filed on Dec. 16, 1992, now Pat. No. 5,413,774, and a continuation-in-part of application No. 08/456,385, filed on Jun. 1, 1995, now Pat. No. 5,658,551, which is a division of application No. 08/315,347, filed on Sep. 30, 1994, now Pat. No. 5,531,980, which is a division of application No. 08/128,540, filed on Sep. 29, 1993, now Pat. No. 5,380,519, which is a division of application No. 07/775,989, filed on Nov. 20, 1991.

(30) Foreign Application Priority Data

Apr. 2, 1990 (EP) .............................. 90810262
Jan. 24, 1992 (EP) .............................. 92810046

(51) Int. Cl.⁷ ................................ A61B 8/00
(52) U.S. Cl. ...................................... 424/9.52
(58) Field of Search .................... 424/9.51, 9.52, 424/450, 489, 499; 128/662.02; 600/458, 441

(56) References Cited

U.S. PATENT DOCUMENTS

| | | |
|---|---|---|
| 3,615,972 A | 10/1971 | Morehouse et al. |
| 3,650,831 A | 3/1972 | Jungermann |
| 3,900,420 A | 8/1975 | Sebba |
| 3,968,203 A | 7/1976 | Spitzer |
| 4,027,007 A | 5/1977 | Messina |
| 4,192,859 A | 3/1980 | Mackaness et al. |
| 4,224,179 A | 9/1980 | Schneider |
| 4,229,360 A | 10/1980 | Schneider |
| 4,235,871 A | 11/1980 | Papahadjopoulos et al. |
| 4,256,251 A | 3/1981 | Moshofsky ................. 227/120 |
| 4,265,251 A * | 5/1981 | Tickner ................. 128/662.01 |
| 4,276,885 A * | 7/1981 | Tickner et al. ......... 128/662.01 |
| 4,316,391 A | 2/1982 | Tickner |
| 4,370,349 A | 1/1983 | Evans |
| 4,442,843 A | 4/1984 | Rasor |
| 4,466,442 A | 8/1984 | Hilmann et al. |
| 4,544,545 A | 10/1985 | Ryan |
| 4,572,203 A | 2/1986 | Feinstein |
| 4,657,756 A | 4/1987 | Rasor |
| 4,681,119 A | 7/1987 | Rasor |
| 4,684,479 A | 8/1987 | D'Arrigo |
| 4,718,433 A | 1/1988 | Feinstein |
| 4,774,958 A | 10/1988 | Feinstein |
| 4,832,941 A | 5/1989 | Berwing |
| 4,844,882 A | 7/1989 | Widder et al. |
| 4,859,363 A | 8/1989 | Davis |
| 4,900,540 A | 2/1990 | Ryan et al. |
| 4,927,623 A | 5/1990 | Long |
| 4,957,656 A | 9/1990 | Cerny |
| 5,049,322 A | 9/1991 | Fessi |
| 5,088,499 A | 2/1992 | Unger |
| 5,089,181 A | 2/1992 | Hauser |
| 5,123,414 A | 6/1992 | Unger |
| 5,137,928 A | 8/1992 | Erbel |
| 5,141,738 A | 8/1992 | Rasor |
| 5,147,631 A | 9/1992 | Glajch et al. |
| 5,149,319 A * | 9/1992 | Unger et al. ................... 604/22 |
| 5,190,982 A | 3/1993 | Erbel |
| 5,195,520 A | 3/1993 | Schlief |
| 5,205,287 A | 4/1993 | Erbel |
| 5,209,720 A | 5/1993 | Unger |
| 5,271,928 A | 12/1993 | Schneider |
| 5,283,067 A | 2/1994 | Geller |
| 5,352,436 A | 10/1994 | Wheatley |
| 5,364,612 A | 11/1994 | Goldenberg |
| 5,380,411 A | 1/1995 | Schlief |

(List continued on next page.)

FOREIGN PATENT DOCUMENTS

| | | |
|---|---|---|
| AU | 40651/89 | 3/1990 |
| AU | 70982/91 | 10/1991 |

(List continued on next page.)

OTHER PUBLICATIONS

Swanson, Pharmaceuticals in Medical Imaging; MacMillan Publishing, NY pp. 682–687 (1990).*

Nomura et al., Jap. J. Med. Ultrasoncis (1991).*

(List continued on next page.)

Primary Examiner—Michael G. Hartley
(74) Attorney, Agent, or Firm—Nixon & Vanderhye P.C.

(57) ABSTRACT

One can impart outstanding resistance against collapse under pressure to gas-filled microvesicle used as contrast agents in ultrasonic echography by using as fillers gases whose solubility in water, expressed in liter of gas by liter of water under standard conditions, divided by the square root of the molecular weight does not exceed 0.003.

10 Claims, 1 Drawing Sheet

U.S. PATENT DOCUMENTS

| | | | |
|---|---|---|---|
| 5,380,519 A | | 1/1995 | Schneider |
| 5,393,524 A | * | 2/1995 | Quay ........................ 424/9.52 |
| 5,409,688 A | | 4/1995 | Quay |
| 5,413,774 A | | 5/1995 | Schneider |
| 5,425,366 A | | 6/1995 | Reinhardt |
| 5,445,813 A | | 8/1995 | Schneider |
| 5,501,863 A | * | 3/1996 | Rössling et al. ............ 424/9.52 |
| 5,527,521 A | * | 6/1996 | Unger ........................ 424/9.3 |
| 5,531,980 A | | 7/1996 | Schneider |
| 5,536,489 A | | 7/1996 | Lohrmann |
| 5,536,490 A | | 7/1996 | Klaveness |
| 5,552,133 A | | 9/1996 | Lambert et al. |
| 5,556,610 A | | 9/1996 | Yan et al. |
| 5,558,856 A | | 9/1996 | Klaveness et al. |
| 5,567,413 A | | 10/1996 | Klaveness |
| 5,567,414 A | | 10/1996 | Schneider |
| 5,593,687 A | | 1/1997 | Rössling et al. |
| 5,599,523 A | | 2/1997 | Beller |
| 5,601,085 A | | 2/1997 | Østensen |
| 5,639,443 A | | 6/1997 | Schutt et al. |
| 5,643,553 A | | 7/1997 | Schneider |
| 5,658,551 A | | 8/1997 | Schneider |
| 5,711,933 A | | 1/1998 | Bichon et al. |
| 5,716,597 A | | 2/1998 | Lohrmann et al. |
| 5,730,954 A | | 3/1998 | Albayrak et al. |
| 5,776,429 A | | 7/1998 | Unger et al. |
| 5,874,062 A | | 2/1999 | Unger |

FOREIGN PATENT DOCUMENTS

| | | |
|---|---|---|
| CA | 1232837 | 2/1988 |
| CA | 1239092 | 7/1988 |
| CA | 2077383 | 3/1993 |
| DE | A 41 27 442 | 2/1993 |
| EP | 0 077 752 | 4/1983 |
| EP | 0122624 | 10/1984 |
| EP | A 131 540 | 1/1985 |
| EP | 0131540 | 10/1985 |
| EP | 0 245 019 | 11/1987 |
| EP | A 324 938 | 7/1989 |
| EP | 0 324 938 | 7/1989 |
| EP | 0324938 | 7/1989 |
| EP | 0327490 | 8/1989 |
| EP | 0441468 | 2/1990 |
| EP | 0357163 | 3/1990 |
| EP | 357 163 | 3/1990 |
| EP | 359 246 A3 | 3/1990 |
| EP | 359 246 A2 | 3/1990 |
| EP | 441 468 | 8/1991 |
| EP | A 458 745 | 11/1991 |
| EP | 0 467 031 A2 | 1/1992 |
| EP | 0494615 | 7/1992 |
| EP | A 554 213 | 4/1993 |
| EP | 0123235 | 10/1994 |
| GB | 1044680 | 10/1966 |
| GB | 213 5647 | 9/1984 |
| NZ | 253115 | 1/1996 |
| WO | WO-A-80/2365 | 11/1980 |
| WO | WO 80/02365 | 11/1980 |
| WO | WO 84/02838 | 8/1984 |
| WO | WO-A-85/02772 | 7/1985 |
| WO | WO 88/7365 | 10/1988 |
| WO | WO 89/05160 | 6/1989 |
| WO | WO 89/06978 | 8/1989 |
| WO | WO 89/10118 | 11/1989 |
| WO | WO 90/01952 | 3/1990 |
| WO | WO 91/09629 | 7/1991 |
| WO | WO91/12823 | 9/1991 |
| WO | WO 91/12823 | 9/1991 |
| WO | WO91/15244 | 10/1991 |
| WO | WO 91/15244 | 10/1991 |
| WO | WO 92/05806 | 4/1992 |
| WO | WO92/05806 | 4/1992 |
| WO | WO 92/17212 | 10/1992 |
| WO | WO A 92/17212 | 10/1992 |
| WO | WO 92/17213 | 10/1992 |
| WO | WO 92/17514 | 10/1992 |
| WO | WO 92/18164 | 10/1992 |
| WO | WO92/18164 | 10/1992 |
| WO | WO 92/19273 | 11/1992 |
| WO | WO 92/21382 | 12/1992 |
| WO | WO 92/22247 | 12/1992 |
| WO | WO 93/5819 | 4/1993 |
| WO | WO93/05819 | 4/1993 |
| WO | WO 93/06869 | 4/1993 |
| WO | WO 93/17718 | 9/1993 |
| WO | WO 94/16739 | 8/1994 |
| ZA | 84/2800 | 4/1984 |

OTHER PUBLICATIONS

Lincoff et al., Arch. Opthamology 98:1610–1611 (1980).*
Lincoff et al., Arch. Opthamology 98:1646 (1980).*
Jacobs, Current Eye Research, 5(8):575–578 (1986).*
Gardner et al., Arch Opthalmol. 106:1188–1189 (1988).*
Dupont Technical Bulletin (El Dupont De Nemours, Wilmington, DE) pp. 1–10 (1987).*
Biochemistry/Ed. Stryer—2 Ed., San Francisco, Freeman, pp. 208–209 (1981).
Concise Encyclopedia Of Polymer Sci. and Engin., Wiley, pp. 12–13 (1990).
Encyclopedia of Polymer Science and Engineering, 2nd ed., 10, p. 95, Wiley & Sons, 1987).
Encyclopedia of Polymer Science and Engineering, pp. 164–169, Wiley & Sons, 1985.
""Freon" Fluorocarbons Properties and Applications," *DuPont Technical Bulletin*, pp. 1–11 (1964).
"Freon" *DuPont Technical Bulletin*, pp. 1–10 (1987).
Gas Encyclopedia, Elsevier Publishier (1976), CCIF3.
Handbook of Pharmaceutical Excipients: Am. Pharm. Ass. 181–183 (1986).
"Lecithin" in Rompp Chemie Kexikon, p. 2474 (1989–92).
"Lecithin" in Blakiston's Gould Medical Dictionary, 4th Ed., N.Y., Mcgraw–Hill,, p. 749 (1979).
"Lecithin" in Dorland's Illustrated Medical Dictionary, 26 Ed., Philadelphia, Saunders, p. 721 (1981).
Remington's Pharmaceutical Sciences: Mack Publ. Comp., 295–298: 736; 1242–44 (1975).
Barnhart et al., *Invest. Radiol*, 25, 162–164 (1990) "Characterics of Albunex".
Benita et al., *Journal of Pharmaceutical Science, 73*, pp. 1721–1724 (1984) "Characterization of Drug Loaded Polydilactide Microspheres".
Bleeker, et al., *J. Acoust. Soc. Am.,* 87 (4), Apr. 1990, pp. 1792–1797, "Ultrasonic characterization of Albune®. . . ".
Bleeker, et al., 1990 *J. Ultrasound Med.,* 9:461–471, (1999), "On the Application of Ultrasonic Contrast Agents . . . ".
Bommer et al., Abstract of the 54 Scient. Sessions, Circulation 64,—203, Abst. 770 (1981).
Crommelin et al., Pharm. Res. pp. 159–163 (1984) "Stability of Liposomes on Storage . . . ".
Crommelin et al., Liposomes as Drug Carriers Symp., pp. 88–93 (1986) "Freezing and Freeze Drying of Liposomes".
de Gruyter, "Phospholipids", *Concise Encyclopedia of Biochemistry,* Berlin, pp. 348–349 (1983).

deJong, et al., *Ultrasonics,* 1992, vol. 30, No. 2, pp. 95–103, "Absorption and scatter of encapsulated gas filled microspheres . . . ".

deJong, et al., *Ultrasonics,* 1991, vol. 29 Jul., pp. 324–330, "Principles and recent developments in ultrasound".

Edwards, et al. *J. Acoust. Soc. Am.,* vol. 70, No. 3 (1983), "Scattering of focused ultrasound by spherical microparticles".

Epstein, et al., *J. Chem. Physics,* vol. 18, No. 11, pp. 1505–1509, Nov. 1950, "On the Stability of Gas Bubbles in Liquid–Gas Solutions".

Feinstein, et al., *JACC,* vol. 16, No. 2, 8/90:316–24, "Safety and Efficacy of a New Transpulmonary Ultrasound Agent . . . ", *Amer. Hearts Assn. Monograph Circulation,* Part II, vol. 72, No. 4, Oct. 1985, *Abstracts of the 58th Scientific Ses.*

Feinsten, et al., *Am. J. of Physiologic Imaging,* 1:12–18 (1986), "Myocardial Contrast Echocardiography . . . ".

Feinstein, *J. of the Amer. Coll. of Cardiol,* 8:251–253 (1986) "Myocardial Perfusion Imaging . . . ".

H. Fessi, et al., "Nanocapsule formation by interfacial polymer deposition . . . ," *Int. J. Pharm.,* 1989, vol. 55, No. 1, pp. R1–R4.

Fieser and Fieser, *Organic Chemistry,* 3rd ed. (1956) p. 847.

Fobbe, et al., *Furtschr Rontgenstr,* 154.3 (1991) 242–245, "Farbkodierte Duplexsonographic und Ultraschallkontrast mittel . . . ".

Ganguly et al., "Structure of hollow polystyrene microspheres . . . " *J. Microencapsulation,* vol. 6, No. 2, 193–198 (1989).

Gardner, et al., (1988), "A Survey of Intraocular Gas Use in North America," *Arch. Ophthalmol.,* 106:1188–1189.

Goldberg et al., *Radiology,* 177, pp. 713–717 (1990) "Hepatic Tumors . . . ".

Helzel, *Fortschr. Rontgenste,* 140, pp. 337–340 (1984) "Erste Erfahrurgen . . . ".

Henry–Michelland et al., *Colloids and Surfaces,* 14, pp. 269–276 (1985) "Lyophilization and Rehydration of Liposomes".

Jacobs, "Intraocular gas measurement using A–scan ultrasound," *Current Eye Research,* vol. 5, No. 8, 1986, pp. 575–578.

Keller et al, *Circulation Res,* 65, 458–467 (1989) "The Behavior of Sonicated Albumin . . . ".

Krause et al., *International Journal of Pharmaceutics.,* 27, pp. 145–155 (1985) "Polylactic acid nanoparticle . . . ".

Levene et al, *J. Acoust. Soc. Am.,* 87 (Suppl) 69 (1990) "Characterization of Albunex . . . ".

Lincoff, et al., Intravitreal Longevity of Three Perfluorocarbon Cases, *Arch. Ophthalmology,* 98:1610–1611 (1980).

Lincoff, et al., "Intravitreal Expansion of Perfluorocarbon Bubbles," *Arch. Ophthalmology,* 98:1646 (1980).

Lincoff, et al., "The Perfluorocarbon Gases in the Treatment of Retinal Detachment," *Ophthalmology,* 90(5):546–551 (1983).

Lincoff, et al., "Perfluoro–n–butane: A Gas for Maximum Duration Retinal Tamponade," *Arch. Ophthalmology,* 101:460–463 (1983).

K. Makino, "Preparation and in vivo degradation properties . . . ," *Chem. Pharm. Bull.,* (1985), vol. 33, No. 3, pp. 1195–1201.

Mattrey et al., *Radiology,* 148, pp. 759–762 (Dec. 1982) "UHM Sound; Perfluoroctylbr omide . . . ".

*Chem Abs.,* vol. 102. No. 3, 21 (Jan. 1985), Maynard et al., "Ultrasonic absorption by liposomes".

Meltzer, et al., *Ultrasound in Med. & Biol.,* vol. 7, No. 4, pp. 377–384, 1981, "Transmission of Ultrasonic Contrast Through the Lungs".

Miller et al., *J. Amer. Soc. Anesthesiol.,* 36 339–351 (1971) "Physicochemical Approaches . . . ".

Möhwald, *Annu. Rev. Phys. Chem.,* 41, 441–76 (1990) "Phospholipid and Phospholipid–Protein Monolayers At The Air/Water Interface".

Murrell et al, "Properties of liquids and solutions", Wiley, p. 276 (1982).

Nomura, et al., "US Contrast Enhancement of Hepatic Tumor with Helium Gas Microbubbles: A Preliminary Report," *Jpn. J. Med. Ultrasonics,* vol. 18, No. 5, 1991, pp. 444–450.

O'Hara et al, *Journal of Membrane Science,* 23 (1985) 1–9, "Preparation of ethylcellulose . . . ".

Ohta, et al., *Jpn. J. Med. Ultrasonics,* vol. 18, No. 4 (1991), "Effect of the Contrast Agent and the Agitation Met".

Ophir, et al., *Ultrasound in Med. & Biol.* vol. 15, No. 4, pp. 319–333, 1989, "Constrast Agents in Diagnostic Ultras".

Ostro in *Spektrum d. Wiss,* 94–95, 98 (Marz 1987). "Liposomen . . . ".

Özer et al., *Acta Pharm. Tech.* 34, pp. 129–139 (1988) "Influence of Freezing and Freeze Drying on Stability of Liposome . . . ".

Park, et al., *Journal of Chemical And Engineering Data,* vol. 27, No. 3 (1982), "Solubility of Gases in Liquids. 14, Bunsen Coefficients for Several Fluorine–Containing Gases (Freons) Dissolved in Water at 298.15K".

Peters et al., *Am. J. Ophthalmol.* 100 pp. 831–839 (1985) "The non expansive, equilibrated concentration of perfluoropropane in the eye".

Puisieux et al., *Bull. Soc. Pharm. Bordeaux,* 123, pp. 111–126 (1984) "Les Liposomes . . . ".

Rompp Lex. Chemie. 8 Aufl. Stuttgart: Franckh; Bd. Z: Cm–G, (1981): BD 3: H–L, (1983): Bd 4, M–Pk (1985) "Porositat".

Schlief, *Current Opinion in Radiology,* 1993, 3:198–207, "Ultrasound Contrast Agents".

Schneider, et al., Investigative Radiol., 26(1), pp. S190–S191 (1991) "A New Ultrasound Contrast Agent Based on Biodegradable Polymers Microballoon".

Schneider, et al., Investigative Radiol., 29(2), pp. S149–S151 (1991) "The Use of Polymers Microballoons as Ultrasound Contrast Agent . . . ".

Swanson, pp. 682–687, "Chapter 22: Enhancement Agents for Ultrasound: Fundamentals," *Pharmaceuticals In Medical Imaging,* (1990).

Szoka et al, *PNAS* 75, pp. 4194–4198 (Sep. 1978) "Procedure for preparation of Liposomes . . . ".

Tomlinson, *Int. J. Pharm. Tech. & Prod. Mfr.,* 4, pp. 49–57 (1983) "Microsphere Delivery Systems . . . ".

Ulmius et al, Biochem., 21, p. 1553 (1982) "Molecular organization . . . ".

K. Uno, et al., "A new method of preparing monocored . . . ," *J. Microencapsulation,* 1984, vol. 1, No. 1, pp. 3–8.

Violante, et al., *Investigative Radiology,* vol. 26, Nov. Supp 1991, "Particle–Stabilized Bubbles for Enhanced Organ Ultrasound Imaging".

Voigt et al., "Lzithine" in Lehrb. d. Pharm. Tech. i, uberarb. Aufl.—Weinheim; VCH, p. 367 (1979).

Wheatley et al, Biomaterials 11, pp. 713–717 (1990) "Contrast agents for diagnostic ultrasound . . . ".

Widder, et al. *AJR:*147, Aug. 1986, "Microbubbles as Contrast Agent for Neurosonography and Ultrasound . . . ".

Zhang, et al., *J. East China Inst. Chem. Tech.,* 12(3) 343–345 (1986) "A Study on the Solubilities of F22 and C2F4 in Aqueous Solutions of HCl and NaCl".

Zeghlouol et al, *Journal de Chimie Physique,* 83: 665–671 (1986) "NMR And Microcalorimetry Study Of The Solubility Of Certain Halons And Their Interaction with Human Serum Albumin".

P.S. Epstein et al., "On the stability of gas bubbles in liquid—gas solutions" *Jour of Chemical Physics,* Nov. 1950, vol. 18 No. 11.

deJong et al Ultrasonics 1992 vol. 30 No. 2 pp. 95–103 Absorption and scatter of encapsulated gas etc.

deJong et al. Ultrasonics 1991 vol. 29 Jul. pp. 324–330 Principles and recent developments in ultrasound etc.

Bleeker et al 1990 J. Ultrasound Med 9:461–471, 1990 pp. 462–471 On the Application of Ultrsonic Contrast etc.

Feinstein et al JACC vol 16, No. 2 8/90:316–24 Safety and Efficacy of a New Transpulmonary Ultrasound etc.

Amer Hearts Assn Monograph Circulation Part II vol. 72 No. 1 10/85 Abstracts of the 58$^{th}$ Scientific Sessions.

Bleeker et al J. Acoust. Soc. Am 87 (4) 4/90 pp. 1792–1797 Ultrasonic Characterization of Albunex® etc.

Epstein et al J. Chem. Physics vol. 18, No. 11, 11/50 On the Stability of Gas Bubbles in Liquid–Gas Solutions.

Meltzer et al Ultrasound in Med & Biol vol. 7, No. 4 pp. 377–384 1981 Trasmission of Ultrasonic Contrast etc.

Violante et al Investigative Radiology vol. 26 Nov. Supp 1991 Particle–Stabilized Bubbles for Enhanced etc.

Ohta et al Jpn J Med Ultrasonics vol. 18 No. 4 (1991) Effect of the Contrast Agent and the Agitation Method etc.

Feinstein et al Am J of Physiologic Imaging 1:12–18 (1986) Myocardial Contrast Echocardiography etc.

Widder et al AJR:147, 8/86 Microbubbles as a Contrast Agent for Neurosonography and Ultrasound– etc.

Schlief Current Opinion in Radiology 1991, 3:198–207 Ultrasound Contrast Agents.

Fobbe et al Furtschr Rontgenstr 154.3 (1991)242–245 Farbkodierte Duplexsonographic und Ultra– etc.

Ophir et al Ultrasound in Med & Biol vol. 15 No. 4 pp. 319–333 1989 Contrast Agents in Diagnostic Ultrasound.

* cited by examiner

LONG-LASTING AQUEOUS DISPERSIONS OR SUSPENSIONS OF PRESSURE-RESISTANT GAS-FILLED MICROVESICLES AND METHODS FOR THE PREPARATION THEREOF

This application is a division of application Ser. No. 08/380,588, filed Jan. 30, 1995, now U.S. Pat. No. 5,578, 292, which is a division of application Ser. No. 07/991,237, filed Dec. 16, 1992, now U.S. Pat. No. 5,413,774, which claims the benefit of EP92810046.0, filed Jan. 24, 1992. This application is also a continuation-in-part of application Ser. No. 08/456,385, filed Jun. 1, 1995, now U.S. Pat. No. 5,658,551, which is a division of application Ser. No. 08/315,347, filed Sep. 30, 1994, now U.S. Pat. No. 5,531, 980, which is a division of application Ser. No. 08/128,540, filed Sep. 29, 1993, now U.S. Pat. No. 5,380,519, which is a division of application Ser. No. 07/775,989, filed Nov. 20, 1991, now U.S. Pat. No. 5,271,928, which is the national stage application of PCT/EP91/00620, filed Apr. 2, 1991, which claims the benefit of EP90810262.7, filed Apr. 2, 1990. This application is also a continuation-in-part of application Ser. No. 08/288,550, filed Aug. 10, 1994, now U.S. Pat. No. 5,711,933, which is a division of application Ser. No. 08/033,435, filed Mar. 18, 1993 and now abandoned, which is a continuation of application Ser. No. 07/695,343, filed May 3, 1991 and now abandoned, which claims the benefit of European Patent No. 90810367.4, filed May 18, 1990.

TECHNICAL FIELD

The present invention concerns stable dispersions or compositions of gas filled microvesicles in aqueous carrier liquids. These dispersions are generally usable for most kinds of applications requiring gases homogeneously dispersed in liquids. One notable application for such dispersions is to be injected into living beings, for instance for ultrasonic echography and other medical applications. The invention also concerns the methods for making the foregoing compositions including some materials involved in the preparations. for instance pressure-resistant gas-filled microbubbles, microcapsules and microballoons.

BACKGROUND OF INVENTION

It is well known that microbodies or microglobules of air or gas (defined here as microvesicles), e.g. microbubbles or microballoons, suspended in a liquid are exceptionally efficient ultrasound reflectors for echography. In this disclosure the term of "microbubble" specifically designates hollow spheres or globules, filled with air or a gas, in suspension in a liquid which generally result from the introduction therein of air or gas in divided form, the liquid preferably also containing surfactants or tensides to control the surface properties and the stability of the bubbles. The term of "microcapsule" or "microballoon" designates preferably air or gas-filled bodies with a material boundary or envelope, i.e. a polymer membrane wall. Both microbubbles and microballoons are useful as ultrasonic contrast agents. For instance injecting into the bloodstream of living bodies suspensions of air-filled microbubbles or microballoons (in the range of 0.5 to 10 $\mu$m) in a carrier liquid will strongly reinforce ultrasonic echography imaging, thus aiding in the visualization of internal organs. Imaging of vessels and internal organs can strongly help in medical diagnosis, for instance for the detection of cardiovascular and other diseases.

The formation of suspensions of microbubbles In an injectable liquid carrier suitable for echography can be produced by the release of a gas dissolved under pressure in this liquid, or by a chemical reaction generating gaseous products, or by admixing with the liquid soluble or insoluble solids containing air or gas trapped or adsorbed therein.

For instance, in U.S. Pat. No. 4,446,442 (Schering), there are disclosed a series of different techniques for producing suspensions of gas microbubbles in a sterilized injectable liquid carrier using (a) a solution of a tenside (surfactant) in a carrier liquid (aqueous) and (b) a solution of a viscosity enhancer as stabilizer. For generating the bubbles, the techniques disclosed there include forcing at high velocity a mixture of (a), (b) and air through a small aperture; or injecting (a) into (b) shortly before use together with a physiologically acceptable gas; or adding an acid to (a) and a carbonate to (b), both components being mixed together just before use and the acid reacting with the carbonate to generate $CO_2$ bubbles; or adding an over-pressurized gas to a mixture of (a) and (b) under storage, said gas being released into microbubbles at the time when the mixture is used for injection.

EP-A-131,540 (Schering) discloses the preparation of microbubble suspensions in which a stabilized injectable carrier liquid, e.g. a physiological aqueous solution of salt. or a solution of a sugar like maltose, dextrose, lactose or galactose, is mixed with solid microparticles (in the 0.1 to 1 $\mu$m range) of the same sugars containing entrapped air. In order to develop the suspension of bubbles in the liquid carrier, both liquid and solid components are agitated together under sterile conditions for a few seconds and, once made, the suspension must then be used immediately, i.e. it should be injected within 5–10 minutes for echographic measurements; indeed, because they are evanescent, the bubble concentration becomes too low for being practical after that period.

In an attempt to cure the evanescence problem. microballoons, i.e. microvesicles with a material wall, have been developed. As said before, while the microbubbles only have an immaterial or evanescent envelope, i.e. they are only surrounded by a wall of liquid whose surface tension is being modified by the presence of a surfactant, the microballoons or microcapsules have a tangible envelope made of substantive material. e.g. a polymeric membrane with definite mechanical strength. In other terms, they are microvesicles of material in which the air or gas is more or less tightly encapsulated.

For instance, U.S. Pat. No. 4,276,885 (Tickner et al.) discloses using surface membrane microcapsules containing a gas for enhancing ultrasonic images, the membrane including a multiplicity of non-toxic and non-antigenic organic molecules. In a disclosed embodiment. these microbubbles have a gelatine membrane which resists coalescence and their preferred size is 5–10 $\mu$m. The membrane of these microbubbles is said to be sufficiently stable for making echographic measurements.

Air-filled microballoons without gelatin are disclosed in U.S. Pat. No. 4,718,433 (Feinstein). These microvesicles are made by sonication (5 to 30 kHz) of protein solutions like 5% serum albumin and have diameters in the 2–20 $\mu$m range, mainly 2–4 $\mu$m. The microvesicles are stabilized by denaturation of the membrane forming protein after sonication, for instance by using heat or by chemical means, e.g. by reaction with formaldehyde or glutaraldehyde. The concentration of stable microvesicles obtained by this technique is said to be about $8\times10^6$/ml in the 2–4 $\mu$m range, about $10^6$/ml in the 4–5 μm range and less than $5×10^5$ in the 5–6 μm range. The stability time of these microvesicles is said to be 48 hrs or longer and they permit convenient left heart imaging after intravenous injection. For instance, the sonicated albumin microbubbles when injected into a peripheral vein are capable of transpulmonary passage. This results in echocardiographic opacification of the left ventricle cavity as well as myocardial tissues.

Recently, still further improved microballoons for injection ultrasonic echography have been reported in EP-A-324.938 (Widder). In this document there are disclosed high concentrations (more than $10^8$/ml) of air-filled protein-bounded microvesicles of less than 10 μm which have life-times of several months or more. Aqueous suspensions of these microballoons are produced by ultrasonic cavitation of solutions of heat denaturable proteins, e.g. human serum albumin, which operation also leads to a degree of foaming of the membrane-forming protein and its subsequent hardening by heat. Other proteins such as hemoglobin and collagen were also said to be convenient in this process. The high storage stability of the suspensions of microballoons disclosed in EP-A-324.938 enables them to be marketed as such, i.e. with the liquid carrier phase, which is a strong commercial asset since preparation before use is no longer necessary.

Similar advantages have been recently discovered in connection with the preparation of aqueous microbubble suspensions, i.e. there has been discovered storage-stable dry pulverulent composition which will generate long-lasting bubble suspensions upon the addition of water. This is being disclosed in Application PCT/EP 91/00620 where liposomes comprising membrane-forming lipids are freeze-dried, and the freeze-dried lipids, after exposure to air or a gas for a period of time, will produce long-lasting bubble suspensions upon simple addition thereto of an aqueous liquid carrier.

Despite the many progresses achieved regarding the stability under storage of aqueous microbubble suspensions, this being either in the precursor or final preparation stage, there still remained until now the problem of vesicle durability when the suspensions are exposed to overpressure, e.g. pressure variations such as that occurring after injection in the blood stream of a patient and consecutive to heart pulses, particularly in the left ventricle. Actually, the present inventors have observed that, for instance in anaesthetised rabbits, the pressure variations are not sufficient to substantially alter the bubble count for a period of time after injection. In contrast, in dogs and human patients, typical microbubbles or microballoons filled with common gases such as air, methane or $CO_2$ will collapse completely in a matter of seconds after injection due to the blood pressure effect. This observation has been confirmed by others: For instance, S. GOTTLIEB et al. in J. Am. Soc. of Echocardiography 3 (1990) 238 have reported that cross-linked albumin microballoons prepared by the sonication method were losing all echogenic properties after being subjected to an overpressure of 60 Torr. It became hence Important to solve the problem and to increase the useful life of suspensions of microbubbles and membrane bounded microballoons under pressure in order to ensure that echographic measurements can be performed in vivo safely and reproducibly.

It should be mentioned at this stage that another category of echogenic Image enhancing agents has been proposed which resist overpressures as they consist of plain microspheres with a porous structure, such porosity containing air or a gas. Such microspheres are disclosed for instance in WO-A-91/12823 (DELTA BIOTECHNOLOGY). EP-A-327 490 (SCHERING) and EP-A-458 079 (HOECHST). The drawback with the plain porous microspheres is that the encapsulated gas-filled free space is generally too small for good echogenic response and the spheres lack adequate elasticity. Hence the preference generally remains with the hollow microvesicles and a solution to the collapsing problem was searched.

DISCLOSURE OF THE INVENTION

This problem has now been solved by using gases or gas mixtures in conformity with the criteria outlined in the claims. Briefly, it has been found that when the echogenic microvesicles are made in the presence of a gas, respectively are filled at least in part with a gas, having physical properties in conformity with the equation below, then the microvesicles remarkably resist pressure >60 Torr after injection for a time sufficient to obtain reproducible echographic measurements:

$$\frac{s_{gas}}{s_{air}} \times \frac{\sqrt{Mw_{air}}}{\sqrt{Mw_{gas}}} \leq 1$$

In the foregoing equation, "s" designates the solubilities in water expressed as the "BUNSEN" coefficients, i.e. as volume of gas dissolved by unit volume of water under standard conditions (1 bar. 25° C.), and under partial pressure of the given gas of 1 atm (see the Gas Encyclopaedia, Elsevier 1976). Since, under such conditions and definitions, the solubility of air is 0.0167, and the square root of its average molecular weight (Mw) is 5.39, the above relation simplifies to:

$$s_{gas}/\sqrt{Mw}_{gas} \leq 0.0031$$

In the Examples to be found hereafter there is disclosed the testing of echogenic microbubbles and microballoons (see the Tables) filled with a number of different gases and mixtures thereof, and the corresponding resistance thereof to pressure increases, both in vivo and in vitro. In the Tables, the water solubility factors have also been taken from the aforecited Gas Encyclopaedia from "L'Air Liquide", Elsevier Publisher (1976).

The microvesicles in aqueous suspension containing gases according to the invention include most microbubbles and microballoons disclosed until now for use as contrast agents for echography. The preferred microballoons are those disclosed in EP-A-324,938, PCT/EP91/01706 and EP-A-458 745; the preferred microbubbles are those of PCT/EP91/00620; these microbubbles are advantageously formed from an aqueous liquid and a dry powder (microvesicle precursors) containing lamellarized freeze-dried phospholipids and stabilizers; the microbubbles are developed by agitation of this powder in admixture with the aqueous liquid carrier. The microballoons of EP-A-458 745 have a resilient interfacially precipitated polymer membrane of controlled porosity. They are generally obtained from emulsions into microdroplets of polymer solutions in aqueous liquids, the polymer being subsequently caused to precipitate from its solution to form a filmogenic membrane at the droplet/liquid interface, which process leads to the initial formation of liquid-filled microvesicles, the liquid core thereof being eventually substituted by a gas.

In order to carry out the method of the present invention, i.e. to form or fill the microvesicles, whose suspensions in aqueous carriers constitute the desired echogenic additives, with the gases according to the foregoing relation, one can either use, as a first embodiment, a two step route consisting of (1) making the microvesicles from appropriate starting materials by any suitable conventional technique in the presence of any suitable gas, and (2) replacing this gas originally used (first gas) for preparing the microvesicles with a new gas (second gas) according to the invention (gas exchange technique).

Otherwise, according to a second embodiment, one can directly prepare the desired suspensions by suitable usual methods under an atmosphere of the new gas according to the invention.

If one uses the two-step route, the initial gas can be first removed from the vesicles (for instance by evacuation under suction) and thereafter replaced by bringing the second gas into contact with the evacuated product, or alternatively, the vesicles still containing the first gas can be contacted with the second gas under conditions where the second gas will displace the first gas from the vesicles (gas substitution). For instance, the vesicle suspensions. or preferably precursors thereof (precursors here may mean the materials the microvesicle envelopes are made of, or the materials which, upon agitation with an aqueous carrier liquid, will generate or develop the formation of microbubbles in this liquid), can be exposed to reduced pressure to evacuate the gas to be removed and then the ambient pressure is restored with the desired gas for substitution. This step can be repeated once or more times to ensure complete replacement of the original gas by the new one. This embodiment applies particularly well to precursor preparations stored dry, e.g. dry powders which will regenerate or develop the bubbles of the echogenic additive upon admixing with an amount of carrier liquid. Hence, in one preferred case where microbubbles are to be formed from an aqueous phase and dry laminarized phospholipids, e.g. powders of dehydrated lyophilized liposomes plus stabilizers, which powders are to be subsequently dispersed under agitation in a liquid aqueous carrier phase, it is advantageous to store this dry powder under an atmosphere of a gas selected according to the invention. A preparation of such kind will keep indefinitely in this state and can be used at any time for diagnosis, provided it is dispersed into sterile water before injection.

Otherwise, and this is particularly so when the gas exchange is applied to a suspension of microvesicles in a liquid carrier phase, the latter is flushed with the second gas until the replacement (partial or complete) is sufficient for the desired purpose. Flushing can be effected by bubbling from a gas pipe or, in some cases, by simply sweeping the surface of the liquid containing the vesicles under gentle agitation with a stream (continuous or discontinuous) of the new gas. In this case, the replacement gas can be added only once in the flask containing the suspension and allowed to stand as such for a while, or it can be renewed one or more times in order to assure that the degree of renewal (gas exchange) is more or less complete.

Alternatively, in a second embodiment as said before, one will effect the full preparation of the suspension of the echogenic additives starting with the usual precursors thereof (starting materials), as recited in the prior art and operating according to usual means of said prior art, but in the presence of the desired gases or mixture of gases according to the invention instead of that of the prior art which usually recites gases such as air, nitrogen, $CO_2$ and the like.

The physiologically acceptable gas is selected from $CF_4$, $CBrF_3$, $CClF_3$, $CCl_2F_2$, $CBrClF_2$, $C_2Cl_2F_4$, $C_2ClF_5$, $C_2F_6$, $C_4F_8$ and $C_4F_{10}$.

It should be noted that in general the preparation mode involving one first type of gas for preparing the microvesicles and, thereafter, substituting the original gas by a second kind of gas, the latter being intended to confer different echogenic properties to said microvesicles, has the following advantage: As will be best seen from the results in the Examples hereinafter, the nature of the gas used for making the microvesicles, particularly the microballoons with a polymer envelope, has a definitive influence on the overall size (i.e. the average mean diameter) of said microvesicles; for instance, the size of microballoons prepared under air with precisely set conditions can be accurately controlled to fall within a desired range, e.g. the 1 to 10 $\mu$m range suitable for echographying the left and right heart ventricles. This not so easy with other gases, particularly the gases in conformity with the requirements of the present invention; hence, when one wishes to obtain microvesicles in a given size range but filled with gases the nature of which would render the direct preparation impossible or very hard, one will much advantageously rely on the two-steps preparation route, i.e. one will first prepare the microvesicles with a gas allowing more accurate diameter and count control, and thereafter replace the first gas by a second gas by gas exchange.

In the description of the Experimental part that follows (Examples), gas-filled microvesicles suspended in water or other aqueous solutions have been subjected to pressures over that of ambient. It was noted that when the overpressure reached a certain value (which is generally typical for a set of microsphere parameters and working conditions like temperature, compression rate, nature of carrier liquid and its content of dissolved gas (the relative importance of this parameter will be detailed hereinafter), nature of gas filler, type of echogenic material, etc.), the microvesicles started to collapse, the bubble count progressively decreasing with further increasing the pressure until a complete disappearance of the sound reflector effect occurred. This phenomenon was better followed optically, (nephelometric measurements) since it Is paralleled by a corresponding change in optical density. i.e. the transparency of the medium increases as the bubble progressively collapse. For this the aqueous suspension of microvesicles (or an appropriate dilution thereof) was placed in a spectrophotometric cell maintained at 25° C. (standard conditions) and the absorbance was measured continuously at 600 or 700 nm, while a positive hydrostatic overpressure was applied and gradually increased. The pressure was generated by means of a peristaltic pump (GILSON's Mini-puls) feeding a variable height liquid column connected to the spectrophotometric cell, the latter being sealed leak-proof. The pressure was measured with a mercury manometer calibrated in Torr. The compression rate with time was found to be linearly correlated with the pump's speed (rpm's). The absorbance in the foregoing range was found to be proportional to the microvesicle concentration in the carrier liquid.

BRIEF DESCRIPTION OF THE DRAWINGS

FIG. 1 shows graphically that the change of absorbance versus pressure is represented by a sigmoid-shaped curve. Up to a certain pressure value, the curve is nearly flat which indicates that the bubbles are stable. Then, a relatively fast absorbance drop occurs, which indicates the existence of a relatively narrow critical region within which any pressure increase has a rather dramatic effect on the bubble count.

Figure 1:
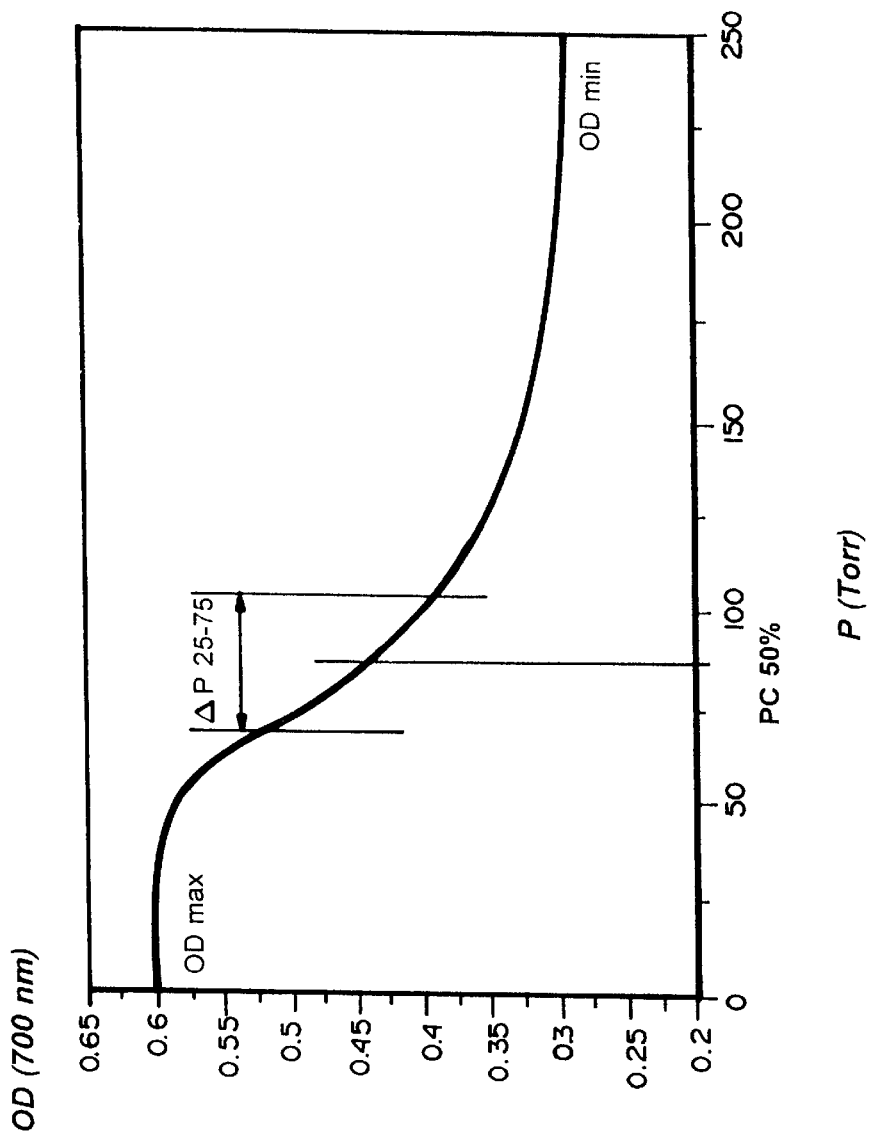
FIG. 1 is a graph which relates the bubble concentration (bubble count), expressed in terms of optical density in the aforementioned range, and the pressure applied over the bubble suspension. The data for preparing the graph are taken from the experiments reported in Example 4.

When all the microvesicles have disappeared, the curve levels off again. A critical point on this curve was selected in the middle between the higher and lower optical readings, i.e. intermediate between the "full"-bubble (OD max) and the "no"-bubble (OD min) measurements, this actually corresponding where about 50% of the bubbles initially present have disappeared, i.e. where the optical density reading is about half the initial reading, this being set, in the graph, relative to the height at which the transparency of the pressurized suspension is maximal (base line). This point which is also in the vicinity where the slope of the curve is maximal is defined as the critical pressure PC. It was found that for a given gas, PC does not only depend on the aforementioned parameters but also, and particularly so, on the actual concentration of gas (or gases) already dissolved in the carrier liquid: the higher the gas concentration, the higher the critical pressure. In this connection, one can therefore increase the resistance to collapse under pressure of the microvesicles by making the carrier phase saturated with a soluble gas, the latter being the same, or not, (i.e. a different gas) as the one that fills the vesicles. As an example, air-filled microvesicles could be made very resistant to overpressures (>120 Torr) by using, as a carrier liquid, a saturated solution of $CO_2$. Unfortunately, this finding is of limited value in the diagnostic field since once the contrast agent is injected to the bloodstream of patients (the gas content of which is of course outside control), it becomes diluted therein to such an extent that the effect of the gas originally dissolved in the injected sample becomes negligible.

Another readily accessible parameter to reproducibly compare the performance of various gases as microsphere fillers is the width of the pressure interval ($\Delta P$) limited by the pressure values under which the bubble counts (as expressed by the optical densities) is equal to the 75% and 25% of the original bubble count. Now, it has been surprisingly found that for gases where the pressure difference $DP=P_{25}-P_{75}$ exceeds a value of about 25–30 Torr, the killing effect of the blood pressure on the gas-filled microvesicles is minimized, i.e. the actual decrease in the bubble count is sufficiently slow not to impair the significance, accuracy and reproducibility of echographic measurements.

It was found, in addition, that the values of PC and $\Delta P$ also depend on the rate of rising the pressure in the test experiments illustrated by FIG. 1, i.e. in a certain interval of pressure increase rates (e.g. in the range of several tens to several hundreds of Torr/min), the higher the rate, the larger the values for PC and $\Delta P$. For this reason, the comparisons effected under standard temperature conditions were also carried out at the constant increase rate of 100 Torr/min. It should however be noted that this effect of the pressure increase rate on the measure of the PC and $\Delta P$ values levels off for very high rates; for instance the values measured under rates of several hundreds of Torr/min are not significantly different from those measured under conditions ruled by heart beats.

Although the very reasons why certain gases obey the aforementioned properties, while others do not, have not been entirely clarified, it would appear that some relation possibly exists in which, in addition to molecular weight and water solubility, dissolution kinetics, and perhaps other parameters, are involved. However these parameters need not be known to practise the present invention since gas eligibility can be easily determined according to the afore-discussed criteria.

The gaseous species which particularly suit the invention are, for instance, halogenated hydrocarbons like the freons and stable fluorinated chalcogenides like $SF_6$, $SeF_6$ and the like.

It has been mentioned above that the degree of gas saturation of the liquid used as carrier for the microvesicles according to the invention has an importance on the vesicle stability under pressure variations. Indeed, when the carrier liquid in which the microvesicles are dispersed for making the echogenic suspensions of the invention is saturated at equilibrium with a gas, preferably the same gas with which the microvesicles are filled, the resistance of the microvesicles to collapse under variations of pressure is markedly increased. Thus, when the product to be used as a contrast agent is sold dry to be mixed just before use with the carrier liquid (see for instance the products disclosed In PCT/EP91/00620 mentioned hereinbefore), it is quite advantageous to use, for the dispersion, a gas saturated aqueous carrier. Alternatively, when marketing ready-to-use microvesicle suspensions as contrast agents for echography, one will advantageously use as the carrier liquid for the preparation a gas saturated aqueous solution; in this case the storage life of the suspension will be considerably increased and the product may be kept substantially unchanged (no substantial bubble count variation) for extended periods, for instance several weeks to several months, and even over a year in special cases. Saturation of the liquid with a gas may be effected most easily by simply bubbling the gas into the liquid for a period of time at room temperature.

EXAMPLE 1

Albumin microvesicles filled with air or various gases were prepared as described in EP-A-324 938 using a 10 ml calibrated syringe filled with a 5% human serum albumin (HSA) obtained from the Blood Transfusion Service, Red-Cross Organization, Bern, Switzerland. A sonicator probe (Sonifier Model 250 from Branson Ultrasonic Corp, USA) was lowered into the solution down to the 4 ml mark of the syringe and sonication was effected for 25 sec (energy setting=8). Then the sonicator probe was raised above the solution level up to the 6 ml mark and sonication was resumed under the pulse mode (cycle=0.3) for 40 sec. After standing overnight at 4° C., a top layer containing most of the microvesicles had formed by buoyancy and the bottom layer containing unused albumin debris of denatured protein and other insolubles was discarded. After resuspending the microvesicles in fresh albumin solution the mixture was allowed to settle again at room temperature and the upper layer was finally collected. When the foregoing sequences were carried out under the ambient atmosphere, air filled microballoons were obtained. For obtaining microballoons filled with other gases, the albumin solution was first purged with a new gas, then the foregoing operational sequences were effected under a stream of this gas flowing on the surface of the solution; then at the end of the operations, the suspension was placed in a glass bottle which was extensively purged with the desired gas before sealing.

The various suspensions of microballoons filled with different gases were diluted to 1:10 with distilled water saturated at equilibrium with air, then they were placed in an optical cell as described above and the absorbance was recorded while increasing steadily the pressure over the suspension. During the measurements, the suspensions temperature was kept at 25° C.

The results are shown in the Table 1 below and are expressed in terms of the critical pressure PC values registered for a series of gases defined by names or formulae, the characteristic parameters of such gases, i.e. Mw and water solubility being given, as well as the original bubble count and bubble average size (mean diameter in volume).

TABLE 1

| Sample | Gas | Mw | Solubility | Bubble count ($10^8$/ml) | Bubble size ($\mu$m) | PC (Torr) | $S_{gas}/\sqrt{Mw}$ |
|---|---|---|---|---|---|---|---|
| AFre1 | $CF_4$ | 88 | .0038 | 0.8 | 5.1 | 120 | .0004 |
| AFre2 | $CBrF_3$ | 149 | .0045 | 0.1 | 11.1 | 104 | .0004 |
| ASF1 | $SF_6$ | 146 | .005 | 13.9 | 6.2 | 150 | .0004 |
| ASF2 | $SF_6$ | 146 | .005 | 2.0 | 7.9 | 140 | .0004 |
| AN1 | $N_2$ | 28 | .0144 | 0.4 | 7.8 | 62 | .0027 |
| A14 | Air | 29 | .0167 | 3.1 | 11.9 | 53 | .0031 |
| A18 | Air | 29 | .0167 | 3.8 | 9.2 | 52 | — |
| A19 | Air | 29 | .0167 | 1.9 | 9.5 | 51 | — |
| AMe1 | $CH_4$ | 16 | .032 | 0.25 | 8.2 | 34 | .008 |
| AKrl | Kr | 84 | .059 | 0.02 | 9.2 | 86 | .006 |
| AX1 | Xe | 131 | .108 | 0.06 | 17.2 | 65 | .009 |
| AX2 | Xe | 131 | .108 | 0.03 | 16.5 | 89 | .009 |

From the results of Table 1, it is seen that the critical pressure PC increases for gases of lower solubility and higher molecular weight. It can therefore be expected that microvesicles filled with such gases will provide more durable echogenic signals in vivo. It can also be seen that average bubble size generally increases with gas solubility.

EXAMPLE 2

Aliquots (1 ml) of some of the microballoon suspensions prepared in Example 1 were injected in the jugular vein of experimental rabbits in order to test echogenicity in vivo. Imaging of the left and right heart ventricles was carried out in the grey scale mode using an Acuson 128-XP5 echography apparatus and a 7.5 MHz transducer. The duration of contrast enhancement in the left ventricle was determined by recording the signal for a period of time. The results are gathered in Table 2 below which also shows the PC of the gases used.

TABLE 2

| Sample (Gas) | Duration of contrast (sec) | PC (Torr) |
|---|---|---|
| AMe1 ($CH_4$) | zero | 34 |
| A14 (air) | 10 | 53 |
| A18 (air) | 11 | 52 |
| AX1 (Xe) | 20 | 65 |
| AX2 (Xe) | 30 | 89 |
| ASF2 ($SF_6$) | >60 | 140 |

From the above results, one can see the existence of a definite correlation between the critical pressure of the gases tried and the persistence in time of the echogenic signal.

EXAMPLE 3

A suspension of echogenic air-filled galactose microparticles (Echovist® from SCHERING AG) was obtained by shaking for 5 sec 3 g of the solid microparticles in 8.5 ml of a 20% galactose solution. In other preparations, the air above a portion of Echovist® particles was evacuated (0.2 Torr) and replaced by an $SF_6$ atmosphere, whereby, after addition of the 20% galactose solution, a suspension of microparticles containing associated sulfur hexafluoride was obtained. Aliquots (1 ml) of the suspensions were administered to experimental rabbits (by injection in the jugular vein) and imaging of the heart was effected as described in the previous example. In this case the echogenic microparticles do not transit through the lung capillaries, hence imaging is restricted to the right ventricle and the overall signal persistence has no particular significance. The results of Table 3 below show the value of signal peak intensity a few seconds after injection.

TABLE 3

| Sample No | Gas | Signal peak (arbitrary units) |
|---|---|---|
| Gal1 | air | 114 |
| Gal2 | air | 108 |
| Gal3 | $SF_6$ | 131 |
| Gal4 | $SF_6$ | 140 |

It can be seen that sulfur hexafluoride, an inert gas with low water solubility, provides echogenic suspensions which generate echogenic signals stronger than comparable suspensions filled with air. These results are particularly interesting in view of the teachings of EP-A-441 468 and 357 163 (SCHERING) which disclose the use for echography purposes of micropartcles, respectively, cavitate and clathrate compounds filled with various gases including SF6; these documents do not however report particular advantages of SF6 over other more common gases with regard to the echogenic response.

EXAMPLE 4

A series of echogenic suspensions of gas-filled microbubbles were prepared by the general method set forth below:

One gram of a mixture of hydrogenated soya lecithin (from Nattermann Phospholipids GmbH, Germany) and dicetyl-phosphate (DCP), in 9/1 molar ratio, was dissolved in 50 ml of chloroform. and the solution was placed in a 100 ml round flask and evaporated to dryness on a Rotavapor apparatus. Then, 20 ml of distilled water were added and the mixture was slowly agitated at 75° C. for an hour. This resulted in the formation of a suspension of multilamellar liposomes (MLV) which was thereafter extruded at 75° C. through, successively, 3 $\mu$m and 0.8 $\mu$m polycarbonate membranes (Nuclepore®). After cooling, 1 ml aliquots of the extruded suspension were diluted with 9 ml of a concentrated lactose solution (83 g/l), and the diluted suspensions were frozen at −45° C. The frozen samples were thereafter freeze-dried under high vacuum to a free-flowing powder in a vessel which was ultimately filled with air or a gas taken from a selection of gases as indicated in Table 4 below. The powdery samples were then resuspended in 10 ml of water as the carrier liquid, this being effected under a stream of the same gas used to fill the said vessels. Suspension was effected by vigorously shaking for 1 min on a vortex mixer.

The various suspensions were diluted 1:20 with distilled water equilibrated beforehand with air at 25° C. and the dilutions were then pressure tested at 25° C. as disclosed in Example 1 by measuring the optical density in a spectrophotometric cell which was subjected to a progressively increasing hydrostatic pressure until all bubbles had collapsed. The results are collected in Table 4 below which, in addition to the critical pressure PC, gives also the $\Delta P$ values (see FIG. 1).

TABLE 4

| Sample No | Gas | $M_w$ | Solubility in $H_2O$ | Bubble count ($10^8$/ml) | PC (Torr) | $\Delta P$ (Torr) |
|---|---|---|---|---|---|---|
| LFre1 | $CF_4$ | 88 | .0038 | 1.2 | 97 | 35 |
| LFre2 | $CBrF_3$ | 149 | .0045 | 0.9 | 116 | 64 |
| LSF1 | $SF_6$ | 146 | .005 | 1.2 | 92 | 58 |

TABLE 4-continued

| Sample No | Gas | $M_w$ | Solubility in $H_2O$ | Bubble count ($10^8$/ml) | PC (Torr) | ΔP (Torr) |
|---|---|---|---|---|---|---|
| LFre3 | $C_4F_8$ | 200 | .016 | 1.5 | 136 | 145 |
| L1 | air | 29 | .0167 | 15.5 | 68 | 17 |
| L2 | air | 29 | .0167 | 11.2 | 63 | 17 |
| LAr1 | Ar | 40 | .031 | 14.5 | 71 | 18 |
| LKr1 | Kr | 84 | .059 | 12.2 | 86 | 18 |
| LXe1 | Xe | 131 | .108 | 10.1 | 92 | 23 |
| LFre4 | $CHClF_2$ | 86 | .78 | — | 83 | 25 |

The foregoing results clearly indicate that the highest resistance to pressure increases is provided by the most water-insoluble gases. The behavior of the microbubbles is therefore similar to that of the microballoons in this regard. Also, the less water-soluble gases with the higher molecular weights provide the flattest bubble-collapse/pressure curves (i.e. ΔP is the widest) which is also an important factor of echogenic response durability in vivo, as indicated hereinbefore.

EXAMPLE 5

Some of the microbubble suspensions of Example 4 were injected to the jugular vein of experimental rabbits as indicated in Example 2 and imaging of the left heart ventricle was effected as indicated previously. The duration of the period for which a useful echogenic signal was detected was recorded and the results are shown in Table 5 below in which $C_4F_8$ indicates octafluorocyclobutane.

TABLE 5

| Sample No | Type of gas | Contrast duration (sec) |
|---|---|---|
| L1 | Air | 38 |
| L2 | Air | 29 |
| LMe1 | $CH_4$ | 47 |
| LKr1 | Krypton | 37 |
| LFre1 | $CF_4$ | >120 |
| LFre2 | $CBrF_3$ | 92 |
| LSF1 | $SF_6$ | >112 |
| LFre3 | $C_4F_8$ | >120 |

These results indicate that, again in the case of microbubbles, the gases according to the criteria of the present invention will provide ultrasonic echo signal for a much longer period than most gases used until now.

EXAMPLE 6

Suspensions of microbubbles were prepared using different gases exactly as described in Example 4, but replacing the lecithin phospholipid ingredient by a mole equivalent of diarachidoylphosphatidylcholine ($C_{20}$ fatty acid residue) available from Avanti Polar Lipids, Birmingham, Ala., USA. The phospholipid to DCP molar ratio was still 9/1. Then the suspensions were pressure tested as in Example 4; the results, collected in Table 6A below, are to be compared with those of Table 4.

TABLE 6A

| Sample No | Type of gas | Mw of gas | Solubility in Water | Bubble count ($10^8$/ml) | PC (Torr) | ΔP (Torr) |
|---|---|---|---|---|---|---|
| LFre1 | $CF_4$ | 88 | .0038 | 3.4 | 251 | 124 |
| LFre2 | $CBrF_3$ | 149 | .0045 | 0.7 | 121 | 74 |
| LSF1 | $SF_6$ | 146 | .005 | 3.1 | 347 | >150 |
| LFre3 | $C_4F_8$ | 200 | .016 | 1.7 | >350 | >200 |
| L1 | Air | 29 | .0167 | 3.8 | 60 | 22 |
| LBu1 | Butane | 58 | .027 | 0.4 | 64 | 26 |
| LAr1 | Argon | 40 | .031 | 3.3 | 84 | 47 |
| LMe1 | $CH_4$ | 16 | .032 | 3.0 | 51 | 19 |
| LEt1 | $C_2H_6$ | 44 | .034 | 1.4 | 61 | 26 |
| LKr1 | Kr | 84 | .059 | 2.7 | 63 | 18 |
| LXe1 | Xe | 131 | .108 | 1.4 | 60 | 28 |
| LFre4 | $CHClF_2$ | 86 | .78 | 0.4 | 58 | 28 |

The above results, compared to that of Table 4, show that, at least with low solubility gases, by lengthening the chain of the phospholipid fatty acid residues, one can dramatically increase the stability of the echogenic suspension toward pressure increases. This was further confirmed by repeating the foregoing experiments but replacing the phospholipid component by its higher homolog, i.e. di-behenoyl-phosphatidylcholine ($C_{22}$ fatty acid residue). In this case, the resistance to collapse with pressure of the microbubbles suspensions was still further increased.

Some of the microbubbles suspensions of this Example were tested in dogs as described previously for rabbits (imaging of the heart ventricles after injection of 5 ml samples in the anterior cephalic vein). A significant enhancement of the useful in-vivo echogenic response was noted. in comparison with the behavior of the preparations disclosed in Example 4, i.e. the increase in chain length of the fatty-acid residue in the phospholipid component increases the useful life of the echogenic agent in-vivo.

In the next Table below, there is shown the relative stability in the left ventricle of the rabbit of microbubbles ($SF_6$) prepared from suspensions of a series of phospholipids whose fatty acid residues have different chain lengths (<injected dose: 1 ml/rabbit).

TABLE 6B

| Phospholipid | Chain length ($C_n$) | PC (Torr) | ΔP (Torr) | Duration of contrast (sec) |
|---|---|---|---|---|
| DMPC | 14 | 57 | 37 | 31 |
| DPPC | 16 | 100 | 76 | 105 |
| DSPC | 18 | 115 | 95 | 120 |
| DAPC | 20 | 266 | 190 | >300 |

It has been mentioned hereinabove that for the measurement of resistance to pressure described in these Examples, a constant rate of pressure rise of 100 Torr/min was maintained. This is justified by the results given below which show the variations of the PC values for different gases in function to the rate of pressure increase. In these samples DMPC was the phospholipid used.

| Gas | PC (Torr) Rate of pressure increase (Torr/min) | | |
|---|---|---|---|
| sample | 40 | 100 | 200 |
| $SF_6$ | 51 | 57 | 82 |
| Air | 39 | 50 | 62 |

-continued

| Gas | PC (Torr) Rate of pressure increase (Torr/min) | | |
|---|---|---|---|
| sample | 40 | 100 | 200 |
| $CH_4$ | 47 | 61 | 69 |
| Xe | 38 | 43 | 51 |
| Freon 22 | 37 | 54 | 67 |

EXAMPLE 7

A series of albumin microballoons as suspensions in water were prepared under air in a controlled sphere size fashion using the directions given in Example 1. Then the air in some of the samples was replaced by other gases by the gas-exchange sweep method at ambient pressure. Then, after diluting to 1:10 with distilled water as usual, the samples were subjected to pressure testing as in Example 1. From the results gathered in Table 7 below, it can be seen that the two-steps preparation mode gives, in some cases, echo-generating agents with better resistance to pressure than the one-step preparation mode of Example 1.

TABLE 7

| Sample No | Type of gas | Mw of the gas | Solubility in water | Initial bubble count ($10^8$/ml) | PC (Torr) |
|---|---|---|---|---|---|
| A14 | Air | 29 | .0167 | 3.1 | 53 |
| A18 | Air | 29 | .0167 | 3.8 | 52 |
| A18/$SF_6$ | $SF_6$ | 146 | .005 | 0.8 | 115 |
| A18/$C_2H_6$ | $C_2H_6$ | 30 | .042 | 3.4 | 72 |
| A19 | Air | 29 | .0167 | 1.9 | 51 |
| A19/$SF_6$ | $SF_6$ | 146 | .005 | 0.6 | 140 |
| A19/Xe | Xe | 131 | .108 | 1.3 | 67 |
| A22/$CF_4$ | $CF_4$ | 88 | .0038 | 1.0 | 167 |
| A22/Kr | Kr | 84 | .059 | 0.6 | 85 |

EXAMPLE 8

The method of the present invention was applied to an experiment as disclosed in the prior art, for instance Example 1 WO-92/11873. Three grams of Pluronic® F68 (a copolymer of polyoxyethylene-polyoxypropylene with a molecular weight of 8400), 1 g of dipalmitoylphosphatidylglycerol (Na salt, AVANTI Polar Lipids) and 3.6 g of glycerol were added to 80 ml of distilled water. After heating at about 80° C., a clear homogenous solution was obtained. The tenside solution was cooled to room temperature and the volume was adjusted to 100 ml. In some experiments (see Table 8) dipalmitoylphosphatidylglycerol was replaced by a mixture of diarachidoylphosphatidylcholine (920 mg) and 80 mg of dipalmitoylphosphatidic acid (Na salt, AVANTI Polar lipids).

The bubble suspensions were obtained by using two syringes connected via a three-way valve. One of the syringes was filled with 5 ml of the tenside solution while the other was filled with 0.5 ml of air or gas. The three-way valve was filled with the tenside solution before it was connected to the gas-containing syringe. By alternatively operating the two pistons, the tenside solutions were transferred back and forth between the two syringes (5 times in each direction), milky suspensions were formed. After dilution (1:10 to 1:50) with distilled water saturated at equilibrium with air, the resistance to pressure of the preparations was determined according to Example 1. The pressure increase rate was 240 Torr/min. The following results were obtained:

TABLE 8

| Phospholipid | Gas | Pc (mm Hg) | DP (mm Hg) |
|---|---|---|---|
| DPPG | air | 28 | 17 |
| DPPG | $SF_6$ | 138 | 134 |
| DAPC/DPPA 9/1 | air | 46 | 30 |
| DAPC/DPPA 9/1 | $SF_6$ | 269 | 253 |

It follows that by using the method of the invention and replacing air with other gases e.g. $SF_6$ even with known preparations a considerable improvements i.e. increase in the resistance to pressure may be achieved. This is true both in the case of negatively charged phospholipids (e.g. DPPG) and in the case of mixtures of neutral and negatively charged phospholipids (DAPC/DPPA).

The above experiment further demonstrates that the recognised problem sensitivity of microbubbles and microballoons to collapse when exposed to pressure i.e. when suspensions are injected into living beings, has advantageously been solved by the method of the invention. Suspensions with microbubbles or microballoons with greater resistance against collapse and greater stability can advantageously be produced providing suspensions with better reproducibility and improved safety of echographic measurements performed in vivo on a human or animal body.

The invention described herein can be further elucidated by the description of the following representative (but not limiting) embodiments, numbered 1–18:

1. A method for imparting resistance against collapsing to contrast agents for ultrasonic echography which consist of gas-filled microvesicles in suspension in aqueous liquid carrier phases, i.e., either microbubbles bounded by an evanescent gas/liquid interfacial closed surface, or microballoons bounded by a material envelope, said collapsing resulting, at least in part, from pressure increases effective, e.g., when the said suspensions are injected into the blood stream of patients, said method comprising forming said microvesicles in the presence of a gas, or if the microvesicles are already made filling them with this gas, which is a physiologically acceptable gas, or gas mixture, at least a fraction of which has a solubility in water expressed in liters of gas by liter of water under standard conditions divided by the square root of the molecular weight in daltons which does not exceed 0.003.

2. The method of embodiment 1, which is carried out in two steps, in the first step the microvesicles or dry precursors thereof are initially prepared under an atmosphere of a first gas, then in the second step at least a fraction of the first gas is substantially substituted by a second gas, the latter being said physiologically acceptable gas.

3. The method of embodiment 1, in which the physiologically acceptable gas used is selected from $SF_6$ or Freon® such as $CF_4$, $CBrF_3$, $C_4F_8$, $CClF_3$, $C_2F_6$, $C_2ClF_5$, $CBrClF_2$, $C_2Cl_2F_4$, and $C_4F_{10}$.

4. The method of embodiment 2, in which the gas used in the first step is a kind that allows effective control of the average size and concentration of the microvesicles in the carrier liquid, and the physiologically acceptable gas added in the second step ensures prolonged useful echogenic life to the suspension for in vivo ultrasonic imaging.

5. The method of embodiment 1, in which the aqueous phase carrying the microbubbles contains dissolved film-forming surfactants in lamellar or laminar form, said surfactants stabilizing the microbubbles boundary at the gas to liquid interface.

6. The method of embodiment 5, in which said surfactants comprise one or more phospholipids.

7. The method of embodiment 6, in which at least part of the phospholipids are in the form of liposomes.

8. The method of embodiment 6, in which at least one of the phospholipids is a diacylphosphatidyl compound wherein the acyl group is a $C_{16}$ fatty acid residue or a higher homologue thereof.

9. The method of embodiments 1 and 2, in which the microballoon material envelope is made of an organic polymeric membrane.

10. The method of embodiment 9, in which the polymers of the membrane are selected from polylactic or polyglycolic acid and their copolymers, reticulated serum albumin, reticulated haemoglobin, polystyrene, and esters of polyglutamic and polyaspartic acids.

11. The method of embodiment 1, in which the forming of the microvesicles with said physiologically acceptable gas is effected by alternately subjecting dry precursors thereof to reduced pressure and restoring the pressure with said gas, and finally dispersing the precursors in a liquid carrier.

12. The method of embodiment 1, in which the filling of the microballoons with said physiologically acceptable gas is effected by simply flushing the suspension with said gas under ambient pressure.

13. The method of embodiment 1, which comprises making the microvesicles by any standard method known in the art but operating under an atmosphere composed at least in part of said gas.

14. Suspensions of gas filled microvesicles distributed in an aqueous carrier liquid to be used as contrast agents in ultrasonic echography, characterized in that the gas is physiologically acceptable and such that at least a portion thereof has a solubility in water, expressed in liter of gas by liter of water under standard conditions, divided by the square root of the molecular weight which does not exceed 0.003.

15. The aqueous suspensions of embodiment 14, characterized in that the gas is such that the pressure difference $\Delta P$ between those pressures which, when applied under standard conditions and at a rate of about 100 Torr/min to the suspension cause the collapsing of about 75%, respectively 25%, of the microvesicles initially present, is at least 25 Torr.

16. Aqueous suspensions according to embodiment 14, in which the microvesicles are microbubbles filled with said physiologically acceptable gas suspended in an aqueous carrier liquid containing phospholipids whose fatty acid residues contain 16 carbons or more.

17. Contrast agents for echography in precursor form consisting of a dry powder comprising lyophilized liposomes and stabilizers, this powder being dispersible in aqueous liquid carriers to form echogenic suspensions of gas-filled microbubbles, characterized in that it is stored under an atmosphere comprising a physiologically acceptable gas whose solubility in water, expressed in liter of gas by liter of water under standard conditions, divided by the square root of the molecular weight does not exceed 0.003.

18. The contrast agent precursors of embodiment 17, in which the liposomes comprise phospholipids whose fatty acid residues have 16 or more carbon atoms.

What is claimed is:

1. A contrast agent for ultrasonic echography having an improved resistance to pressure variations comprising, as a suspension in an aqueous carrier liquid, microballoons consisting of a freon gas bounded by an organic polymer envelope made from denatured serum albumin.

2. A contrast agent for ultrasonic echography having an improved resistance to pressure variations comprising, as a suspension in an aqueous carrier liquid, microballoons consisting of a freon gas bubble encapsulated by an organic polymer envelope made from denatured serum albumin.

3. A contrast agent for ultrasonic echography having an improved resistance to pressure variations comprising, as a suspension in an aqueous carrier liquid, microballoons comprising a freon gas bubble encapsulated by an organic polymer envelope made from denatured serum albumin, said envelope being in contact only with the gas and the aqueous carrier liquid.

4. A contrast agent for ultrasonic echography having resistance to pressure variations comprising:
   a) a plurality of polymeric structures, each polymeric structure consisting of denatured serum albumin in a hollow microballoon form,
   b) a freon gas that is contained within the hollow microballoon form, and
   c) an aqueous pharmaceutical formulation for injection.

5. A contrast agent for ultrasonic echography having resistance to pressure variations comprising:
   a) a plurality of polymeric structures, each polymeric structure consisting of denatured serum albumin,
   b) a freon gas that is contained within the polymeric structure, and
   c) an aqueous pharmaceutical formulation for injection.

6. A contrast agent for ultrasonic echography comprising, as a suspension in an aqueous carrier liquid, microballoons consisting of a gas comprising a halogenated hydrocarbon bounded by an organic polymer envelope made from denatured serum albumin.

7. A contrast agent for ultrasonic echography comprising, as a suspension in an aqueous carrier liquid, microballoons consisting of a gas bubble comprising a halogenated hydrocarbon encapsulated by an organic polymer envelope made from denatured serum albumin.

8. A contrast agent for ultrasonic echography comprising, as a suspension in an aqueous carrier liquid, microballoons consisting of a gas bubble comprising a halogenated hydrocarbon encapsulated by an organic polymer envelope made from denatured serum albumin, said envelope being in contact only with the gas and the aqueous carrier liquid.

9. A contrast agent for ultrasonic echography having resistance to pressure variations comprising:
   a) a plurality of polymeric structures, each polymeric structure consisting of denatured serum albumin in a hollow microballoon form,
   b) gas comprising a halogenated hydrocarbon that is contained within the hollow microballoon form, and
   c) an aqueous pharmaceutical formulation for injection.

10. A contrast agent for ultrasonic echography comprising:
   a) a plurality of polymeric structures, each polymeric structure consisting of denatured serum albumin,
   b) gas comprising a halogenated hydrocarbon that is contained within the polymeric structure, and
   c) an aqueous pharmaceutical formulation for injection.

* * * * *